United States Patent [19]

Galber

[11] Patent Number: 5,057,656

[45] Date of Patent: Oct. 15, 1991

[54] SAFETY CONTAINER FOR USED SYRINGES, PROVIDED WITH MEANS FOR REMOVING THE NEEDLES FROM THE SYRINGE BODY

[76] Inventor: Maria A. Galber, Via Biancamano, 14, 20052 Monza, Milano, Italy

[21] Appl. No.: 269,989

[22] Filed: Nov. 10, 1988

[30] Foreign Application Priority Data

Nov. 11, 1987 [IT] Italy .............................. 22602 A/87

[51] Int. Cl.$^5$ ........................................... B65D 83/10
[52] U.S. Cl. ................................. 206/366; 220/908
[58] Field of Search ........................................ 206/366

[56] References Cited

U.S. PATENT DOCUMENTS 4,674,676  6/1987  Sandel et al. ...................... 206/366
4,714,168 12/1987  Johnson et al. ..................... 206/366
4,722,472  2/1988  Bruno ................................ 206/366

*Primary Examiner*—Joseph Man-Fu Moy

[57] ABSTRACT

The present invention relates to a safety container for used syringes, provided with means for removing from the syringe body the needles, even if these needles are screw engaged on the syringe body.

The container essentially consists of a boxlike body, having a tiltable cover and provided, at the top surface thereof and said cover, with suitably shaped openings.

The mentioned box-like body is made by folding on itself, starting from its flat configuration, and according preset folding lines, a suitably die-cut and ribbed element made of any suitable rigid materials.

2 Claims, 1 Drawing Sheet

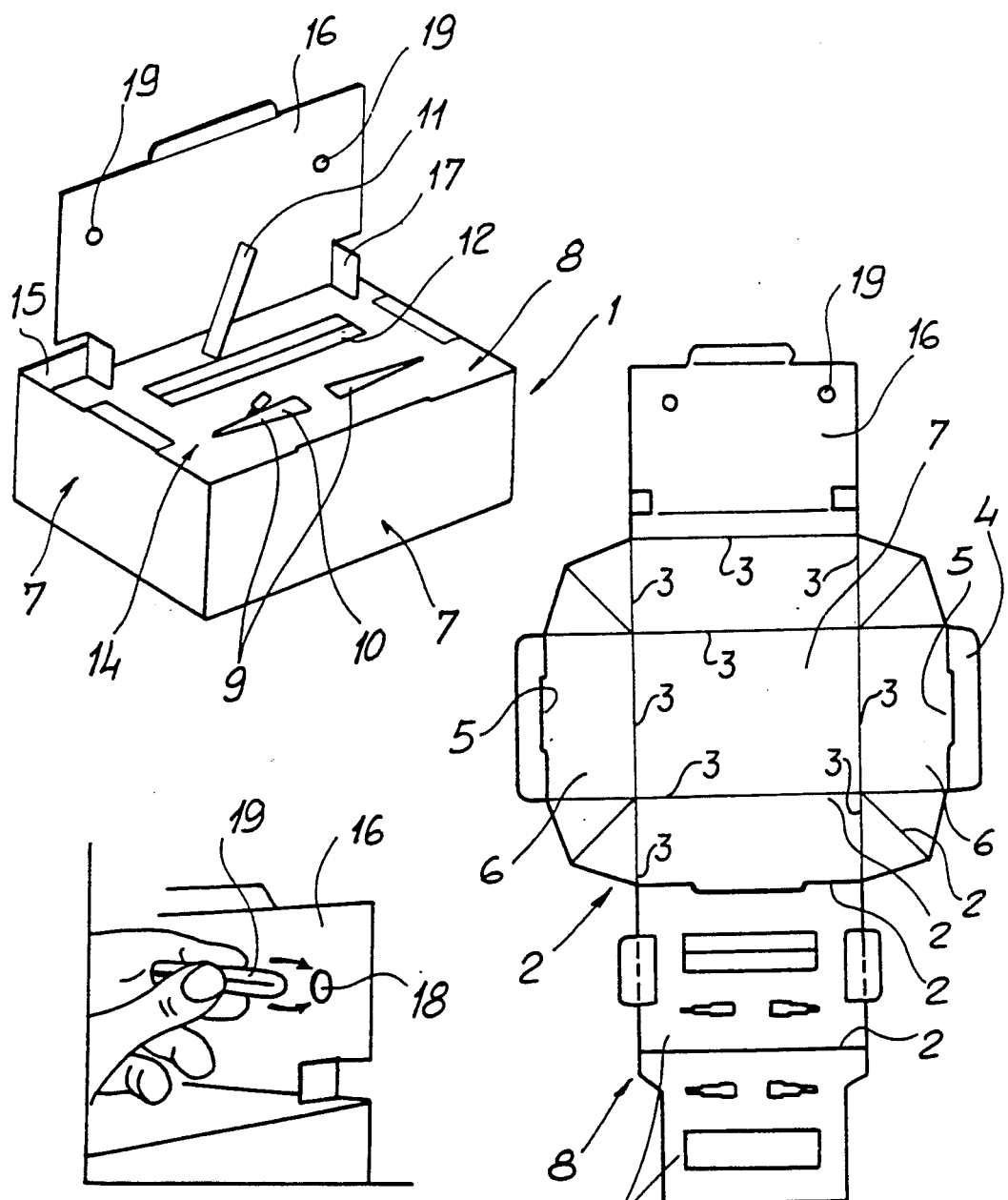

SAFETY CONTAINER FOR USED SYRINGES, PROVIDED WITH MEANS FOR REMOVING THE NEEDLES FROM THE SYRINGE BODY

BACKGROUND OF THE INVENTION

The present invention relates to a safety container for used syringes, provided with means for removing from the syringe body the needles, even if these needles are screw-engaged on said syringe body.

As is known, syringes and related needles, after use are usually randomly rejected and put in collecting boxes or the like which, on the other hand, are not specifically designed for such a disposal.

This fact, as it should be apparent, represents a source of possible damages, in the case of a not proper handling of the used syringes, both to the sanitary operator and to possible users of the sanitary or ambulatorial organization.

Like drawbacks, moreover, may occur at the urban solid waste collecting places, thereto there are frequently conveyed sanitary wastes which, on the other hand, should be discharged at specifically designed discharing places adapted for receiving toxic or damaging wastes.

SUMMARY OF THE INVENTION

Accordingly, the task of the present invention is to overcome the above mentioned drawbacks, by providing a container for used syringes which comprises means for easily removing the needles from the syringe bodies, without the need of carrying out manual operations.

Within the scope of the above mentioned task, a main object of the present invention is to provide a used syringe container which comprises means for easily and safely removing from the syringe bodies screw-engaged needles like those which are frequently used in analysis and the like laboratories.

Another object of the present invention is to provide such a used syringe container which assures a great safety during the insertion of a needle into a related needle cover.

According to one aspect of the present invention, the above mentioned task and objects, as well as yet other objects, which will become more apparent hereinafter, are achieved by a safety container for used syringes provided with means for removing from the syringe bodies the syringe needles, even if said needles are screw-engaged to said syringe bodies, characterized in that said container comprises a box-like body having a tiltable cover and provided, at its top surface and cover, with suitably shaped openings, said box-like body being made by folding on itself, starting from its flat configuration, and along preset folding lines, a suitably die-cut and ribbed element, made of a suitably rigid material.

BRIEF DESCRIPTION OF THE DRAWINGS

Further characteristics and advantages of the safety container for used syringes according to the present invention, will become more apparent hereinafter from the following detailed description of a preferred embodiment of said container which is illustrated, by way of a merely indicative and not limitative example, in the figures of the accompanying drawing, in which:

FIG. 1 shows a perspective view of the container according to the invention;

FIG. 2 shows the extended flat configuration of the sheet element forming the container according to the invention; and FIG. 3 shows a detail of the tiltable cover associated with the subject container.

DESCRIPTION OF THE PREFERRED EMBODIMENT

With reference to the figures of the accompanying drawing, the used syringe safety container according to the invention, which has been overally indicated at the reference number 1, is made starting from a suitably die-cut element 2, of any suitable rigid materials (preferably cardboard or thick card-board) which is folded on itsself, starting from its flat extended configuration, according to preset folding lines 3.

During the assembling of the subject container, suitable wings 4 arranged on the sides of the mentioned element 2, are engaged in corresponding seats 5, formed in suitable flaps 6, so as to define a box-shaped body and, in its inside, a recess adapted to operate as a containing or holding space.

In this connection it should be pointed out that between the faces 7 which are coupled to one another in the above mentioned way, a sufficient binding is provided for the intended use.

More specifically, the top face or surface 8 is provided with cuts 9, for example two cuts in an exemplary embodiment, having preferably a triangular shape, and in which the needle end portion 10 of a syringe 11 may be fitted.

By a subsequent small rotation or tearing operation, carried out by the user, the mentioned needle end portion is separated by the syringe body arranged in a hand of the user.

The top surface 8 of the box or container is further provided with a rectangular shape cut 12, thereinto the syringe body can be introduced, after having removed therefrom the needle end portion.

The top surface 8 of the box or container, in particular, consists of two portions 13, which, in the extended condition of the element 2 are arranged in an adjoining relationship, which portions are folded onto one another so as to provide a strong top panel 14 adapted to facilitate the detaching of the needle 10.

The box-like body 1 is moreover provided, at an edge 15 of its top surface 8, with a lug 16 having a suitable shaped flap which can be folded so as to operate as a closure cover for the container.

The cover 16 is provided, at the end portions of the mentioned edge 15, with two small die-cut flaps 17, adapted to be inwardly folded so as to support said cover, as it is opened, and adapted to be returned to a flat condition as the boxlike body must be closed, in order to convey it to the waste collecting place or container.

The cover further comprises one or more round througoing holes 18, for circumferentially restrain a needle covering element 19.

The provision of this holes, practically affords the possibility of operating in a complete safe way even for removing from the syringe body screw engaged needle.

In this connection it should be pointed out that, owing to the mentioned approach, the user will be safely protected against possible damages as the needle is engaged with or disengaged from the syringe body.

To this end, in fact, it will be sufficient to screw on the needle to the syringe body, remove the needle covering element and insert it into one of the holes formed through the cover.

Then, after having used the needle, the user will resinsert it, in its condition mounted on the syringe, into the needle covering element (restrained in one of the mentioned holes), while screwing off the needle assembly from the syringe body without removing the needle covering element from the container cover.

Thus, the fingers of the user will be safely protected, since the mentioned container cover will operate as a proper barrier.

Then, after having removed the syringe body, the needle covering element-needle assembly can be easily caused to drop, by a simple pressure, into the box-like body for disposal of the waste.

From the above disclosure it should be apparent that the container according to the invention affords the possibility of greatly reducing, during the post-use handling, the risks of possible damagings associated with possible contacts with infect needles.

Another advantage of the container according to the invention is that it has a very reduced cost.

While the used syringe container according to the invention has been disclosed and illustrated with reference to a preferred embodiment thereof, it should be apparent that the disclosed embodiment is susceptible to many modifications and variations all of which will come within the spirit and scope of the invention as defined in the accompanying claims.

I claim:

1. A safety container for used syringes comprising a box like body having a top surface, a bottom surface and side surfaces, a tiltable cover covering said top surface and openings through said top surface and cover, said box-like body being made by folding a flat die-cut rigid material element including a plurality of performed folding lines, wherein said openings of said top surface comprise at least a triangular opening therein a needle tip portion of a syringe can be engaged for separating said needle tip portion from said syringe and at least a rectangular opening therethrough a syringe body can pass to be introduced into said container, whereas said openings through said cover comprise at least a round hole adapted to circumferentially restrain a needle covering element so as to easily unthread a syringe needle from a said syringe body.

2. A container according to claim 1, wherein said cover is provided with two small die-cut flaps adapted to be inwardly folded to abut against said top surface so as to hold said cover in a raised condition as said cover is open and adapted to be returned to a flat condition as said cover is closed to close said box-like body.

* * * * *